United States Patent [19]
Selby et al.

[11] Patent Number: 5,660,362
[45] Date of Patent: Aug. 26, 1997

[54] PIVOTING LEVELING STAND

[75] Inventors: Theodore W. Selby, Midland; Michael A. Tubbs, Zeeland; Robert H. Seer, Midland; Gregory C. Müller, Midland; Kevin J. Wolfe, Midland, all of Mich.

[73] Assignee: Tannas Co., Midland, Mich.

[21] Appl. No.: 643,853

[22] Filed: May 7, 1996

Related U.S. Application Data

[63] Continuation of Ser. No. 425,617, Apr. 20, 1995, abandoned.

[51] Int. Cl.⁶ .................................................. F16M 11/24
[52] U.S. Cl. ........................................ 248/188.4; 248/650

[56] References Cited

U.S. PATENT DOCUMENTS

| | | | |
|---|---|---|---|
| 3,358,951 | 12/1967 | Carter | 248/650 |
| 3,442,150 | 5/1969 | Brawner et al. | 248/481 |
| 3,609,014 | 9/1971 | Kurz, Jr. | 248/481 |
| 4,156,323 | 5/1979 | Scheffler | 248/516 |
| 4,185,917 | 1/1980 | Alsina | 248/481 |
| 4,298,248 | 11/1981 | Lapp | 248/481 |
| 4,796,791 | 1/1989 | Goss et al. | 248/650 |
| 5,239,361 | 8/1993 | Burch | 356/345 |
| 5,436,769 | 7/1995 | Gilbert et al. | 248/481 |

OTHER PUBLICATIONS

ASTM D 2983-87, Reapproved 1993.
Brookfield Viscometers/Rheometers Catalog, Brookfield Engineering Laboratories, Inc., Stoughton, Mass., 1993, pp. 3,7,12,21 & 22.

Primary Examiner—Leslie A. Braun
Assistant Examiner—Willie Berry, Jr.
Attorney, Agent, or Firm—Christopher John Rudy

[57] ABSTRACT

Pivoting leveling stand has a base with an outer, horizontal boundary; a pivot, downward of and in contact with the base, and positioned inwardly of the outer horizontal boundary of the base; and at least three leveling machines in contact with the base placed outwardly of the pivot. The pivot is capable of contacting an underlying support surface, and the leveling machines are attachable to an underlying support. As an option, from the base, preferably above the pivot, a fixture, for example, an upright rod such as for attaching a sensitive rotating viscometer, may be attached to the stand.

13 Claims, 2 Drawing Sheets

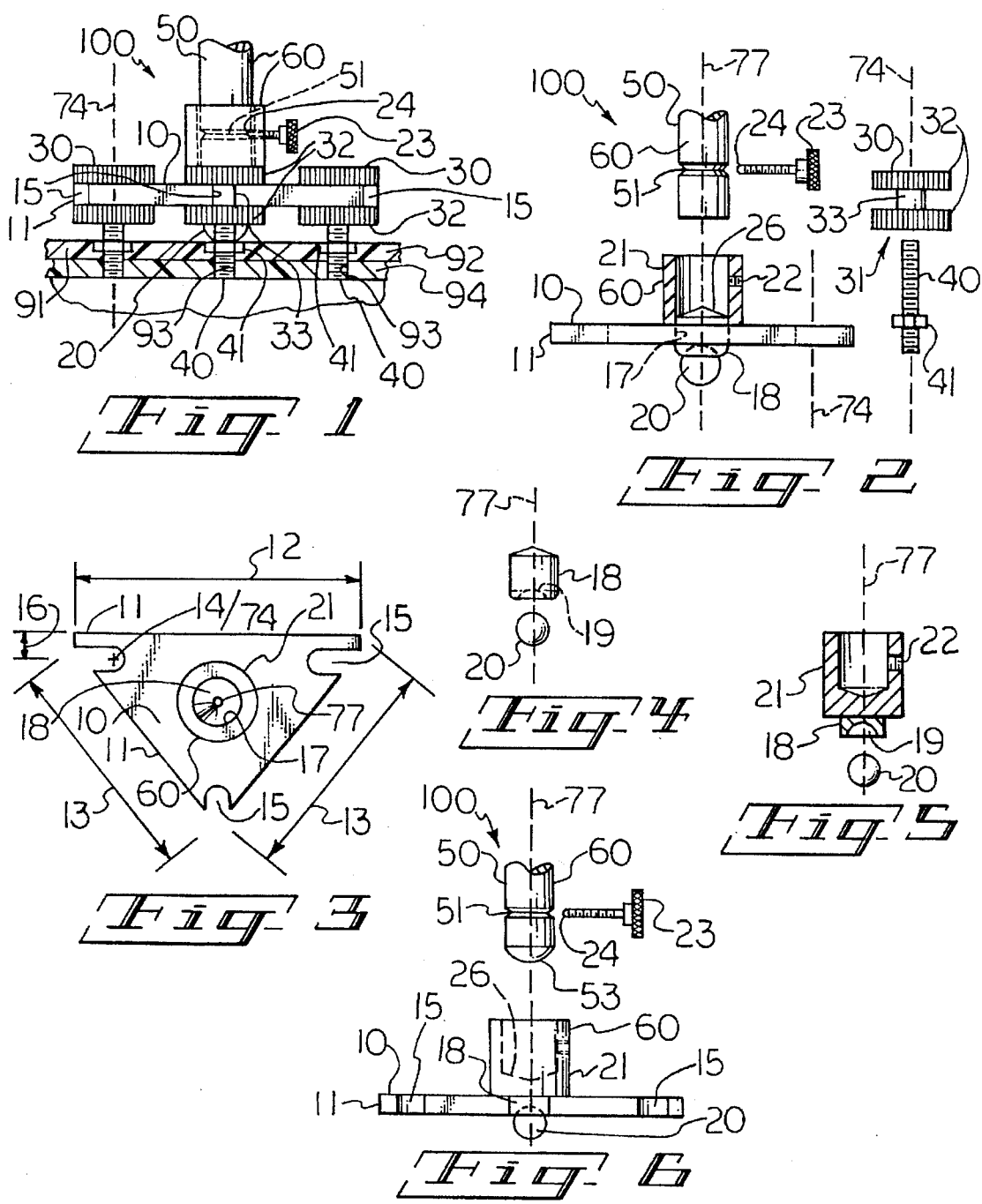

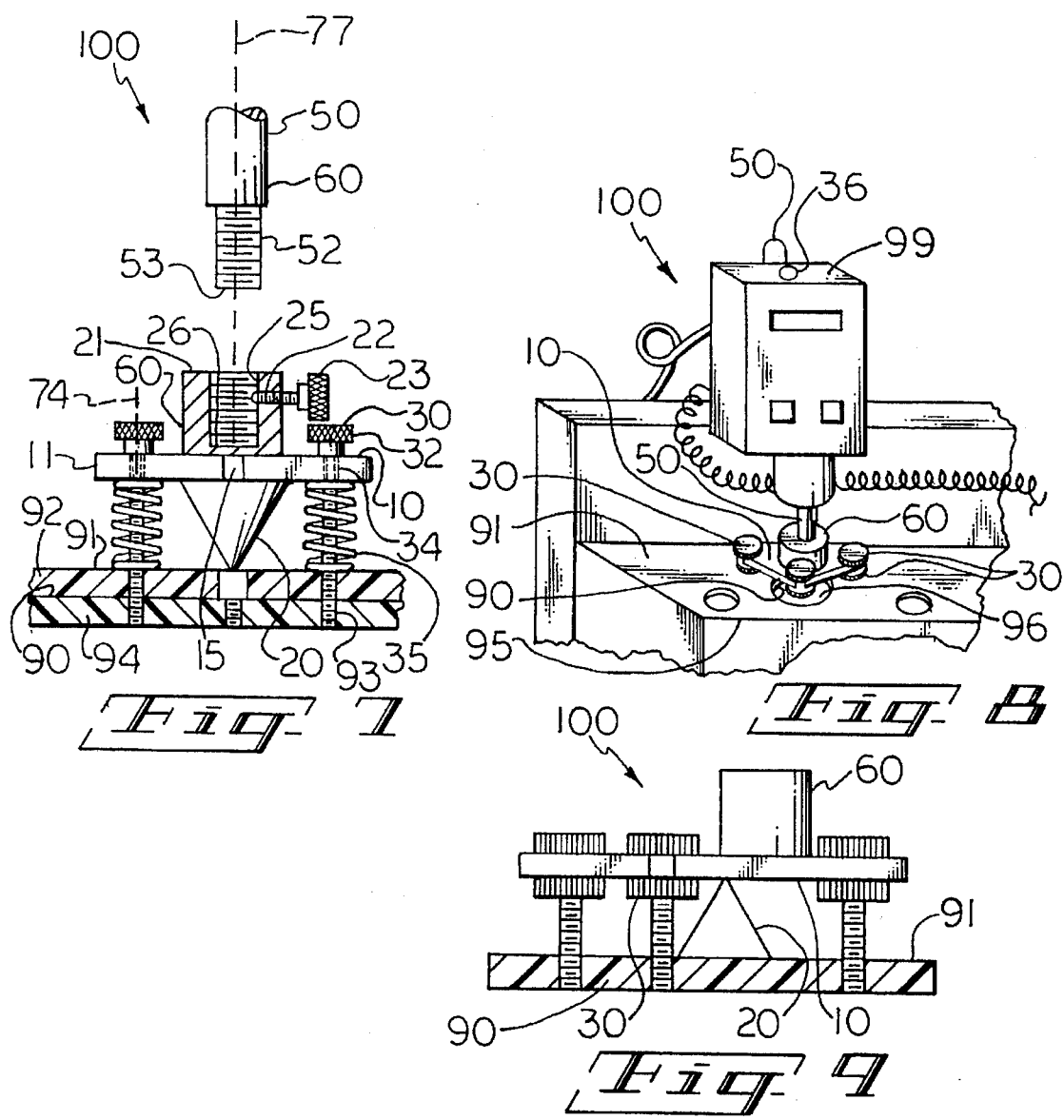

5,660,362

1

PIVOTING LEVELING STAND

This is a continuation of application Ser. No. 08/425617, filed Apr. 20, 1995, now abandoned.

FIELD

The present invention concerns a stand for leveling. In a particular embodiment, it also concerns supporting a sensitive rotating viscometer, useful in viscosity testing.

BACKGROUND

Rotational viscometers require a rotating element called the rotor and a stationary element called the stator, which contains the fluid to be tested for properties such as viscosity, and in which most typically the rotor rotates in contact with the fluid so as to determine drag caused by the liquid. This drag can then be related to the viscosity.

Sensitive rotational viscometers such as the Brookfield viscometer are well-known instruments for measuring viscosities of liquids. Usually, the rotor, which is driven by a motor in the Brookfield head, is immersed in a large container of liquid in which the walls of the container are at some considerable distance from the rotor and thus have little influence on the measurement of the viscous value. This container is the stator. In some applications such as in the well-known ASTM D 2983, which tests the viscosity of gear oil at low temperature, the rotor must be radially and vertically aligned to gain the necessary accuracy. What is more, since the apparent viscosity of the tested fluid, a factor of the amount of torque or drag exerted on the rotor by the fluid in contact with it, is proportional to the extent to which the rotor is immersed in the fluid, any vertical, i.e., up and down, movement of the rotor in the test fluid will alter the torque and thus the viscosity readout. Thus, the instrument must be balanced carefully and supported firmly, not only from radial displacement but also especially from vertical movement.

In practice, problems are encountered with commercially available Brookfield viscometers such as the so-called "Top Hat" type viscometer, which is known commercially as the Brookfield Dial Reading Viscometer, and Brookfield Digital Display Viscometer, DV- & LV-series models. In particular, the fine balance required for the ASTM D 2983 test can be hard to acquire so as to obtain accurate results, and there often is encountered unacceptable vertical movement with the instrument, to make for additionally inaccurate readout.

What is needed is an improvement which overcomes such problems, while providing for precise radial and vertical balance of the sensitive rotating viscometer and its rotor. It should be readily manufacturable and commercializable—and efficient to operate, even by inexperienced operators. Desirably, it might also be applicable in further fields.

SUMMARY

The present invention provides a pivoting leveling stand comprising a base having an outer, horizontal boundary, optionally on which base a fixture, for example, an upright rod such as for attaching a sensitive rotating viscometer, is attachable; a pivot, downward of and in contact with the base, and positioned inwardly of the outer horizontal boundary of the base, the pivot being capable of contacting an underlying support surface; and at least three leveling machines in contact with the base placed outwardly of the pivot and attachable to an underlying support.

The invention is useful in leveling.

2

Significantly, by the invention, problems in the art are solved or ameliorated. In particular, exceedingly fine radial and vertical balance can be provided the sensitive rotating viscometer and its rotor spindle while maintaining a firm emplacement of the same such that the accuracy of fluid viscosity testing, for example, in accordance with the ASTM D 2983 protocol, is perceptibly improved in kind. The invention is readily manufacturable and commercializable—and efficient to operate, by even inexperienced operators. Also, the invention may be applicable in other fields.

Numerous further advantages attend the invention.

DRAWINGS

The drawings form part of the specification hereof. In the drawings, in which like numerals refer to like features, the following is briefly noted:

FIG. 1 is front partially cut-away side view of a pivoting leveling stand of the invention as in contact with and attached to a top of a temperature control bath housing for viscometry testing.

FIG. 2 is an exploded partially cut away side view of the stand, with one leveling machine depicted, as of FIG. 1.

FIG. 3 is top view of the base of the stand, without leveling machines, as of FIG. 1.

FIG. 4 is an exploded side view of a rod stop and pivot of the stand as of FIG. 1.

FIG. 5 is an exploded partially cut away side view of another embodiment of a rod stop and pivot of a pivoting leveling stand hereof.

FIG. 6 is an exploded partially cut away side view of a pivoting leveling stand of the invention, without leveling machines, as generally taken with parts of FIG. 5.

FIG. 7 is an exploded partially cut away side view of another embodiment of a pivoting leveling stand of the invention, with a front leveling machine absent, as in contact with and attached to a top of a temperature control bath housing for viscometry testing.

FIG. 8 is a perspective view of a pivoting leveling stand of the invention, to which is attached a sensitive rotational viscometer, and which stand is in contact with and attached to the top of a temperature control bath housing for viscometry testing.

FIG. 9 is a side view of another embodiment hereof.

ILLUSTRATIVE DETAIL

The invention can be further understood by reference to certain particular embodiments, which, although they may be related to viscometer art, are not necessarily of themselves to be construed as so limiting in nature.

Thus, in further reference to the drawings, in general, pivoting leveling stand 100 has base 10, which may be of any suitable shape, to include planar circles, non-circular ellipses, triangles, rectangles, and so forth, or be of various suitable non-planar embodiments, and which has outer, horizontal boundary 11. Pivot 20, which may be of any suitable shape, to include spherical, conical, pyramidal, and so forth, is downward of and in contact with the base 10, and placed inwardly of the outer, horizontal base boundary 11. The pivot 20 may be in contact with the base 10 in any suitable manner, to include by being attached or affixed to or even integral with the base, or by being in friction contact therewith such as by being held in place by the weight of the base, and so forth. At least three leveling machines 30, which may be of any suitable construction, to include with screws, hydraulic, pneumatic, magnetic, and/or mechanical lifts such as jacks, friction, and so forth, are in contact with the base 10 and are placed outwardly of the pivot 20. The pivot 20 can contact top surface 91 of underlying support 90 while leveling machines 30 are attachable to the underlying support 90. The pivot 20 may be in contact with the underlying support 90 in any suitable manner, to include by being in friction contact therewith such as by being held in place by the weight of the base 10 and pivot 20, or by being attached or affixed to or even integral with the underlying support 90, and so forth. From the base 10 a fixture 60, to include, for example, upright rod 50 for attaching a sensitive rotating viscometer 99 may be attached. Preferably, any such attachment would occur above the pivot 20.

The stand may be made of any suitable material such as of a suitable metal, engineering plastic, wood, stone, and so forth and the like. Its components may vary in materials and construction, and may be made through casting, molding, drilling, threading, tapping, welding, brazing, soldering, gluing, and so forth as those skilled in the art appreciate.

For example, base 10 can be made of ¼-inch (ca. 0.63 cm) stainless steel plate, which is machined to provide, in general, isosceles triangle shaped base with an about 5-inch (ca. 11.7 cm) longer side dimension 12, and two about 3-inch (ca. 7.6 cm) shorter side dimensions 13. A ½-inch (ca. 1.27 cm) hole is centered at point 14, and ½-inch wide slot 15 is then provided to have depth 16 from boundary 11 to point 14 along leveling axis 74. Central hole 17 of, say, ⅝-inch (ca. 1.46 cm) diameter, may be provided for about central axis 77 for, say, ⅝-inch wide stub 18 having concave recess 19 to accept ½-inch ball bearing pivot Rod collar 21 adapted to hold the upright rod 50 extends upwardly from the base 10. As depicted, the upright rod 50 can be attached directly above the pivot 20. In the case of materials such as stainless steel, silver soldering or the like can be employed to connect component parts such as base 10, stub 18, ball bearing pivot 20, and/or rod collar 21. The stub 18 may be initially separate from the rod collar 21 (FIGS. 2 & 4), or it may be made as one piece therewith (FIGS. 5 & 6). Alternatively, base 10, pivot 20, which may be generally conical, and which, as with the pivot 20 made with a ball bearing (FIGS. 1–6), has a generally spherical surface which contacts the underlying support surface 91, and rod collar 21 may be cast or molded together as one piece (FIG. 7). As another alternative, the rod 50 may be cast or molded as one piece therewith. Another alternative has the pivot 20 being inverted (FIG. 9) with it, as for example, being adjustable to appropriate positions not only on the underlying support surface 91 but also under the base 10. Further, machining such as by drilling and cutting to provide the slots 15 and drilling and tapping to provide female threads 22 for rod set screw 23 can be carried out as necessary or desired. The rod set screw may have conical tip 24 for insertion in V-shaped slot 51 of upright rod 50, and/or rod collar 21 may have female threads 25 for accepting suitable upright rod 50 having male threads 52. Rod bottom 53 may be flat (FIGS. 2 & 7) or shaped such as with a turned radius (FIG. 6) for a more suited or close registration with rod collar floor 26. Three leveling machines 30 of the screw type are depicted in general, which can be stacked-dual-headed nuts 31 of, say, brass. Each such nut 31 has two heads 32 connected with a center post 33, is tapped for female threads to go along leveling machine center axis 74, and envelope the base 10, top and bottom. Each may screw onto male-threaded studs 40 set into underlying support 90. In one embodiment, the studs 40 pass through ¼-inch top layer 92 of, say, an acrylic-polyvinylchloride alloy as the well known KYDEX-100 acrylic-polyvinylchloride alloy, are screwed into tapped holes 93 to go along leveling machine center axis 74 in ¼-inch subsurface layer 94 of, say, aluminum, and are set with jam nuts 41 in the top layer 92. Optional Concave Recess 97 may be present in top layer 92 to accommodate pivot 20. The underlying support 90 can be part of viscometer bath housing 95. In an alternate depicted embodiment, the leveling machine 39 is also of the screw type, having a single brass head 32 attached to a steel threaded shaft 34, which screws into tapped hole 93 to go along leveling machine center axis 74 in ¼-inch subsurface layer 94 of, say again, aluminum. Suitably stiff springs 35 help steady the stand.

Further components may be present in accord herewith.

In operation, the pivoting leveling stand is employed to provide a known surface orientation, based on the desired orientation of the base 10 and/or fixture 60, preferably which is level or based on an alternate orientation related to levelness, which is determined by suitable means such as leveling bubbles, transits, lasers, and so forth. In the viscometry art, for example, the pivoting leveling stand, which may be termed a pivoting viscometer leveling stand, is attached to a suitable viscometer and leveled by suitable means. Thus, a sensitive rotational viscometer 99 can be attached to upright rod 50 attached to or part of pivoting viscometer leveling stand 100, and the assembly leveled, according to a leveling device such as a bubble in liquid leveling device 36 attached to the top of the viscometer 99, and steadied by use of leveling machines 30 while pivot 20 is in contact with top surface 91 of underlying support 90 while leveling machines 30 are attached to the underlying support 90 as part of viscometer bath housing 95 in which stator hole 96 provides access to a temperature control bath for regulation of sample temperature during viscosity tests.

CONCLUSION

The present invention is thus provided. Numerous modifications can be effected within its spirit, the literal claim scope of which is particularly pointed out as follows:

We claim:

1. A pivoting viscometer leveling stand comprising a base having an outer, horizontal boundary; a pivot, downward of and in contact with the base and positioned inwardly as the outer horizontal boundary of the base, the pivot being capable of contacting an underlying support surface; and three leveling machines in contact with the base placed outwardly of the pivot and attachable to an underlying support, said stand being adaptable for supporting and finely balancing a sensitive rotating viscometer for fluid viscosity testing, wherein a rod collar which can hold an upright rod capable of supporting said viscometer is present directly above the pivot.

2. The stand or claim 1, wherein an upright rod, capable of supporting said viscometer, is attached directly above the pivot through the rod collar.

3. The stand of claim 2, wherein the leveling machines are of the screw type.

4. The stand of claim 2, wherein the pivot is attached to the base.

5. The stand of claim 1, wherein the pivot has a generally spherical surface for contacting the underlying support surface.

6. A pivoting leveling stand comprising a base having an outer, horizontal boundary; a pivot, downward of and in contact with the base, and positioned inwardly of the outer horizontal boundary of the base, the pivot being capable of contacting an underlying support surface; and at least three leveling machines in contact with the base placed outwardly of the pivot and attachable to an underlying support, wherein a fixture is attachable on the base, and the leveling machines are of the screw type and have stacked-dual-headed nut heads which envelope the base, top and bottom.

7. The stand of claim 6, wherein the nut heads screw onto studs attached to the underlying support.

8. The stand of claim 7, with three leveling machines.

9. The stand of claim 6, with three leveling machines.

10. A pivoting viscometer leveling stand comprising a base having an outer, horizontal boundary; a pivot, downward of and in contact with the base, and positioned inwardly of the outer horizontal boundary of the base, the pivot being capable of contacting an underlying support surface; and at least three leveling machines in contact with the base placed outwardly of the pivot and attachable to an underlying support, wherein an upright rod is present which is attachable directly above the pivot through a rod collar, and the leveling machines are of the screw type and have nut heads which envelope the base, top and bottom.

11. The stand of claim 10, wherein the nut heads screw onto studs attached to the underlying support.

12. The stand of claim 11, with three leveling machines.

13. The stand of claim 10, with three leveling machines.

* * * * *